(12) United States Patent
Ariola, Jr.

(10) Patent No.: US 7,621,911 B2
(45) Date of Patent: Nov. 24, 2009

(54) DISPOSABLE/REMOVABLE TUBING SET FOR USE WITH AN ELECTROSURGICAL INSTRUMENT

(75) Inventor: John P. Ariola, Jr., Norton, MA (US)

(73) Assignee: Kirwan Surgical Products, Inc., Marshfield, MA (US)

( * ) Notice: Subject to any disclaimer, the term of this patent is extended or adjusted under 35 U.S.C. 154(b) by 510 days.

(21) Appl. No.: 11/412,553

(22) Filed: Apr. 27, 2006

(65) Prior Publication Data

US 2007/0255272 A1 Nov. 1, 2007

(51) Int. Cl.
*A61B 18/18* (2006.01)

(52) U.S. Cl. .......................... 606/51; 606/52; 606/210; 606/211

(58) Field of Classification Search ............. 606/51, 606/52, 210, 211, 45–50; 604/22
See application file for complete search history.

(56) References Cited

U.S. PATENT DOCUMENTS

| | | | | |
|---|---|---|---|---|
| 3,395,711 A | * | 8/1968 | Plzak, Jr. | 128/200.26 |
| 4,096,864 A | * | 6/1978 | Kletschka et al. | 604/35 |
| 4,188,871 A | * | 2/1980 | Teachout | 100/2 |
| 4,562,838 A | * | 1/1986 | Walker | 606/42 |
| 4,578,059 A | * | 3/1986 | Fabricant et al. | 604/43 |
| 5,019,038 A | * | 5/1991 | Linden | 604/540 |
| 5,055,100 A | | 10/1991 | Olsen | 604/22 |
| 5,085,657 A | | 2/1992 | Ben-Simhon | 606/42 |
| 5,088,997 A | | 2/1992 | Delahuerga et al. | 606/42 |
| 5,154,709 A | | 10/1992 | Johnson | 606/45 |
| 5,181,916 A | * | 1/1993 | Reynolds et al. | 606/16 |
| 5,250,075 A | * | 10/1993 | Badie | 606/207 |
| 5,312,327 A | | 5/1994 | Bales et al. | 604/21 |
| 5,336,220 A | * | 8/1994 | Ryan et al. | 604/22 |
| 5,451,222 A | | 9/1995 | De Maagd et al. | 606/41 |
| 5,549,547 A | | 8/1996 | Cohen et al. | 604/30 |
| 5,558,650 A | * | 9/1996 | McPhee | 604/218 |
| 5,624,393 A | * | 4/1997 | Diamond | 604/48 |
| 5,674,219 A | | 10/1997 | Monson et al. | 606/45 |
| 5,704,925 A | | 1/1998 | Otten et al. | 604/272 |
| 6,030,356 A | * | 2/2000 | Carlson et al. | 604/22 |
| D426,883 S | | 6/2000 | Berman et al. | D24/112 |
| 6,228,084 B1 | * | 5/2001 | Kirwan, Jr. | 606/52 |
| 6,298,550 B1 | * | 10/2001 | Kirwan, Jr. | 29/825 |
| 6,749,610 B2 | * | 6/2004 | Kirwan et al. | 606/51 |
| 6,764,487 B2 | | 7/2004 | Mulier et al. | 606/41 |
| 7,122,035 B2 | * | 10/2006 | Canady | 606/52 |
| 7,322,907 B2 | * | 1/2008 | Bowser | 482/121 |
| 7,402,754 B2 | * | 7/2008 | Kirwan et al. | 174/110 R |

OTHER PUBLICATIONS

Pamphlet—SAF T VAC Smoke & Fluid Evacuator, Surgiform Plastic and Cosmetic Surgery Products.

* cited by examiner

*Primary Examiner*—Linda C Dvorak
*Assistant Examiner*—Amanda Scott
(74) *Attorney, Agent, or Firm*—Weingarten, Schurgin, Gagnebin & Lebovici LLP

(57) ABSTRACT

A tubing set attaches to an electrosurgical instrument having one or more tines to provide irrigation. The tubing set includes a length of tubing having a connector fitting on the proximal end to connect to a fluid source. A distal end of the tubing connects to a nose piece that attaches to the tine of the electrosurgical instrument, thereby providing irrigation to the instrument.

23 Claims, 3 Drawing Sheets

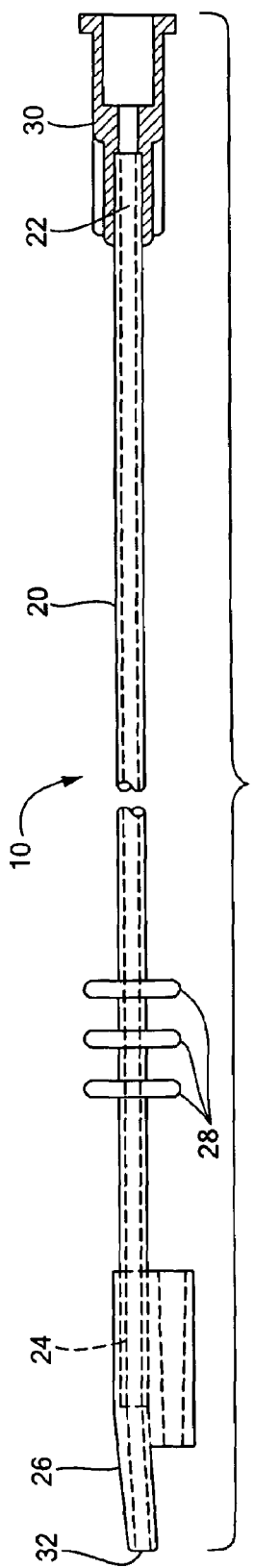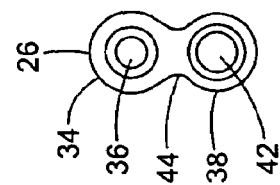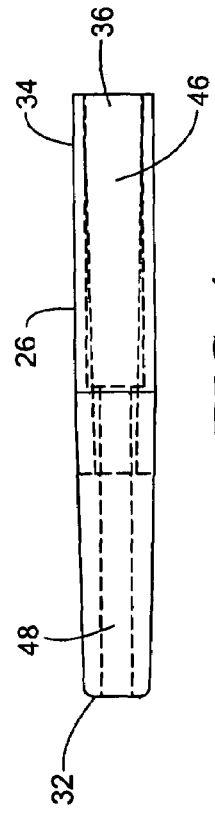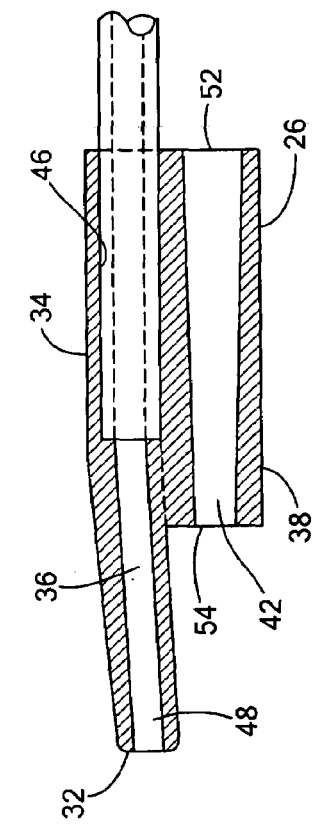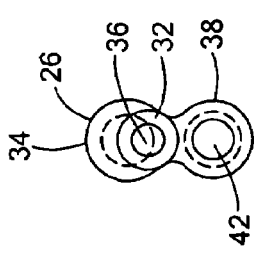

DISPOSABLE/REMOVABLE TUBING SET FOR USE WITH AN ELECTROSURGICAL INSTRUMENT

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

A variety of electrosurgical devices are available for performing different surgical procedures. For example, coagulation procedures require an instrument that is capable of coagulating tissue to stop or minimize the flow of blood at the surgical site. Such instruments may also be capable of flushing an irrigation solution into the area where the surgeon is working to remove bits of tissue or blood. In other alternatives, these instruments may be capable of aspirating fluids from the site. Such fluids include liquids, such as saline solution or blood, and gases, such as smoke or air.

For example, electrosurgical forceps have a pair of tines or blades that are used to grasp and coagulate tissue. The forceps may be monopolar or bipolar. In monopolar forceps, one or both of the tines form an electrode in electrical communication with an electrical generator. Current flows from the active electrode through the patient's tissue to a dispersive electrode in contact with the patient's skin, which may be at some distance from the forceps, and back to the generator. In bipolar forceps, each tine of the pair comprises an electrode in communication with the electrical generator.

In some forceps, an irrigation channel is formed along one or both of the tines to allow an irrigation fluid, such as saline solution, to flow through the channel and out the outlet near the tip of the tines to flush bits of tissue or blood away from the area where the surgeon is working. See, for example, U.S. Pat. No. 6,228,084. In another known type of bipolar coagulating instrument, a pair of electrodes is arranged coaxially. A suction channel is provided along the central axis to draw fluids away from the surgical site. See, for example, U.S. Pat. Nos. 5,989,249 and 6,406,476. Not all coagulating instruments are, however, formed with an irrigation or aspiration channel or channels.

SUMMARY OF THE INVENTION

The present invention relates to a tubing set for attachment to an electrosurgical instrument having one or more tines to add an irrigation capability to the instrument. The tubing set includes a length of tubing extending between a distal end and a proximal end. A connector fitting on the proximal end is configured to connect to a fluid source. The distal end of the tubing is affixed to a nose piece that attaches to a tine of the instrument.

More particularly, the nose piece includes a fluid portion and a tine portion. A tine passage extends through the tine portion for receiving the distal end of a tine of the electrosurgical instrument. A fluid passage extends through the fluid portion. The distal end of the tubing is affixed within at least a first section of the fluid passage. A second section of the fluid passage is preferably angled downwardly toward the tine to direct fluid onto the tip of the tine.

In one preferred embodiment, the inventive tubing set can be attached with a luer fitting to a standard IV tubing set, such as for use with an IV solution to deliver, for example, saline solution from a bag to the instrument.

DESCRIPTION OF THE DRAWINGS

The invention will be more fully understood from the following detailed description taken in conjunction with the accompanying drawings in which:

FIG. 2 is a partially broken away side view of the tubing set of FIG. 1;

FIG. 3 is a side view of a nose piece of the tubing set of FIG. 1;

FIG. 4 is a top view of the nose piece of FIG. 3;

FIG. 5 is a left end view of the nose piece of FIG. 3;

FIG. 6 is a right end view of the nose piece of FIG. 3;

DETAILED DESCRIPTION OF THE INVENTION

Figure 1:
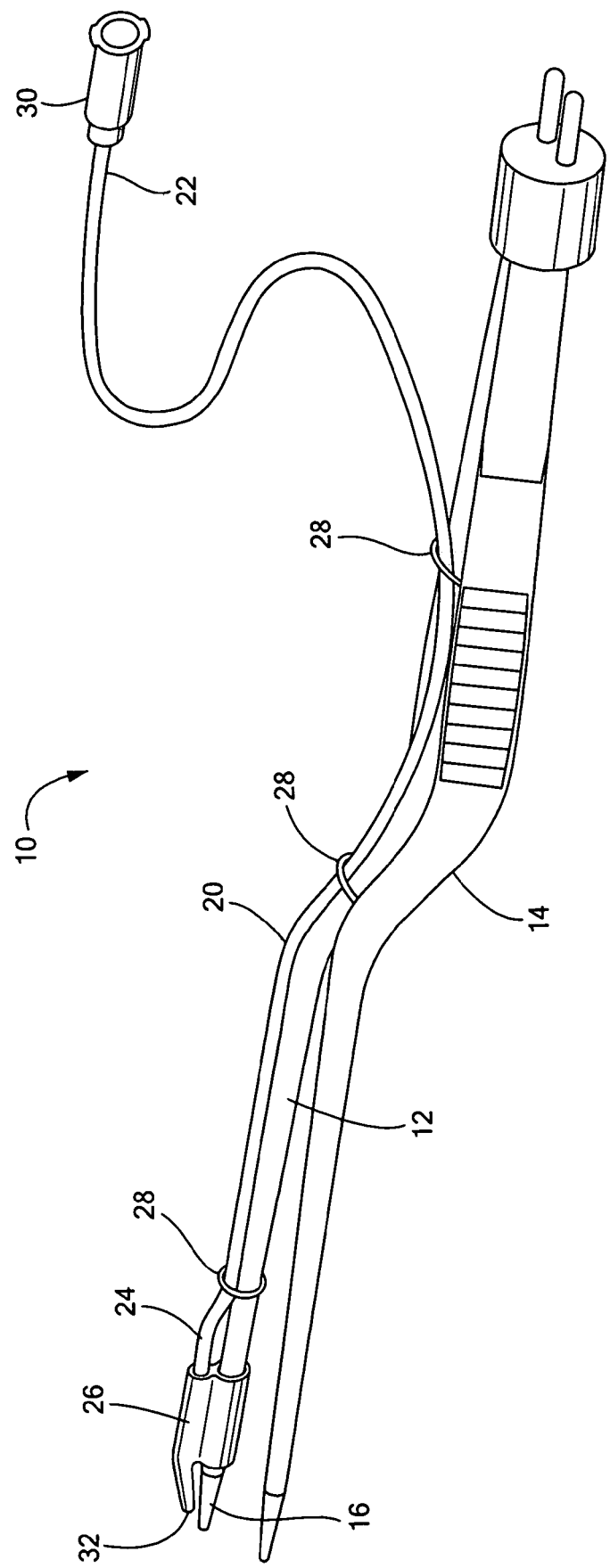
FIG. 1 is an isometric view of a tubing set in accordance with the present invention in conjunction with an electrosurgical coagulating forceps.

A tubing set 10 according to the present invention is illustrated in FIGS. 1 and 2. In the embodiment illustrated, the tubing set is attached to one tine 12 of a non-irrigating electrosurgical coagulating forceps 14. The tubing set is connectable to a source of fluid, such as saline solution, to deliver fluid to drip onto the tip 16 of the tine, resulting in a device capable of providing irrigation.

More particularly, the tubing set includes a length of tubing 20 that extends from a proximal end 22 to a distal or instrument end 24. The instrument end of the tubing is affixed within a nose piece 26. The nose piece is attached to the tip 16 of a tine 12 of an electrosurgical forceps 14. The tubing is held along the length of the tine by any suitable mechanism, such as O-rings 28. The proximal end of the tubing terminates at a suitable fitting 30 for connection to a fluid source. In the embodiment illustrated, the proximal end is connected to a female luer fitting.

In the embodiment illustrated, the forceps 14 do not include an irrigation channel. Thus, the tubing set 10 of the present invention allows a user such as a surgeon to add the option of irrigation to this type of forceps. Toward this end, one of the tines 12 of the forceps is slipped through the O-rings 28 on the length of tubing, and the nose piece 26 of the tubing set is placed over the tip 16 of the tine. The O-rings are adjusted along the tine so that the tubing is retained along most of the length of the tine out of the surgeon's way. The tubing set is connected to a source of fluid, such as saline solution for irrigation.

The tubing 20 is made of any suitable flexible plastic material, such as PVC. The tubing may be of any suitable length. In the embodiment illustrated, an 18-inch length from the nose piece 26 to the luer fitting 30 is suitable. The proximal end 22 of the tubing is attached to the fitting 30 in any suitable manner. For example, the proximal end can be attached to the luer fitting with a suitable medical grade adhesive. In this case, the O-rings 28 are placed over the length of tubing prior to installing the luer fitting. The O-rings are made of any suitable material, such as a medical grade silicone. The O-rings provide flexibility and adjustment to allow the tubing to be placed along a forceps tine of any length.

The nose piece 26 is preferably made of the same flexible plastic material as the tubing 20. The flexibility of the material allows the nose piece to stretch up onto the tapered tine and up over the insulation if present on the tine. The nose piece grips the tine so that the most distal end 32 of the nose piece can be adjusted into the proper location for the proper irrigant flow.

Referring to FIGS. 3-6, the nose piece 26 includes a fluid portion 34 having a fluid passage 36 therethrough and a tine portion 38 having a tine passage 42 therethrough. The fluid portion and the tine portion are interconnected by, for example, a web member 44 integral with the fluid portion and the tine portion. The fluid passage 36 includes a first section 46 into which the distal end of the tubing is inserted. Preferably, the tubing is affixed within the first portion in any suitable manner, such as by insert molding. The fluid passage includes a second section 48 that has a smaller inner diameter than the inner diameter of the first section. The inner diameter of the second section is preferably the same inner diameter as the tubing. The second section is also preferably angled downwardly at a small angle (e.g., 6°) toward the tip of the tine when the nose piece is placed over the tine. In this way, fluid is directed toward and onto the tine.

The tine passage 42 is preferably tapered from a wider diameter at the proximal or tine entry end 52 to the distal or tine exit end 54 to accommodate the taper of the tine. The flexibility of the material allows the nose piece to be adjustable along the tip of the tine. The nose piece grips the tine to hold the tubing in place. By adjusting the location of the nose piece on the tine's tip, the irrigation fluid can drip onto the forceps tip where required. The surface tension of the irrigation fluid keeps the fluid attached to the tip until it drips away.

Figure 7:
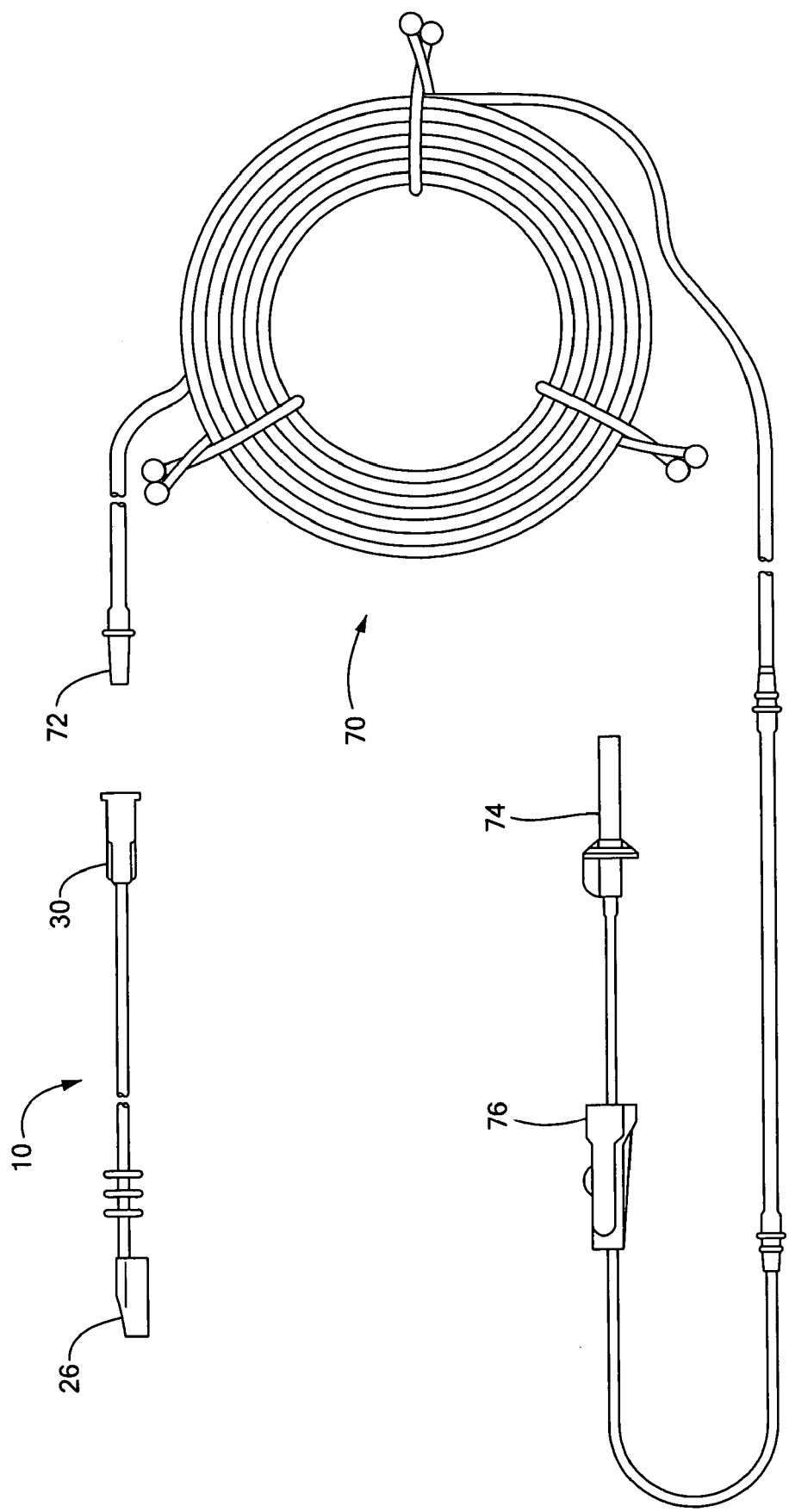
FIG. 7 is a plan view of the tubing set of FIG. 1 in conjunction with a standard tubing set.

FIG. 7 illustrates a tubing set 10 of the present invention in conjunction with a standard tubing set 70. The proximal end of the inventive tubing set is attached via the female luer fitting 30 to a male luer fitting 72 on a distal end of the standard tubing set. The proximal end of the standard tubing set includes a connection 74 to a source of fluid, such as a spike that connects to a bag of saline solution. The fluid flow rate can be regulated by, for example, a roller clamp 76. Alternatively, the tubing set can be connected to an irrigation pump to control the fluid flow.

The tubing set can be used with a variety of forceps. The forceps can be insulated or uninsulated, disposable or reusable. The nose piece can be attached to either tine of the forceps. Alternatively, two tubing sets can be used, one attached to each tine, resulting in a dual irrigation device. In a still further alternative, in a forceps having one irrigating tine and one non-irrigating tine, the tubing set can be attached to the non-irrigating tine, again resulting in a dual irrigation device. The tubing set can also be used with an instrument having a single tine, blade, or probe.

The invention is not to be limited by what has been particularly shown and described, except as indicated by the appended claims.

What is claimed is:

1. A tubing set for attachment to an electrosurgical instrument having one or more tines, comprising:
    a length of tubing extending between a distal end and a proximal end, the tubing formed of a flexible plastic material, a connector fitting on the proximal end configured to connect to a fluid source;
    a unitary nose piece comprising:
        a fluid portion and a tine portion,
        the tine portion having an elongated tubular tine passage extending therethrough and through which a distal end of a tine of the electrosurgical instrument is slidably insertable,
        the fluid portion having an elongated tubular fluid passage extending therethrough,
        at least a first section of the fluid passage in overlaying alignment with at least a portion of the tine passage, and
        a second section of the fluid passage angled downwardly to direct fluid flowing through the fluid passage toward the tip of the tine when the tine is inserted through the tine passage; and
    the distal end of the tubing inserted into the first section of the fluid passage.

2. The tubing set of claim 1, further comprising a further mechanism to hold a portion of the length of the tubing to most of the length of the tine spaced proximally from the nose piece.

3. The tubing set of claim 2, wherein the mechanism comprises one or more O-rings circumferentially surrounding the tubing and the tine.

4. The tubing set of claim 3, wherein the one or more O-rings are adjustable along the length of the tine.

5. The tubing set of claim 1, wherein the fluid portion of the nose piece further comprises a second section of the fluid passage having a smaller inner diameter than the first section of the fluid passage.

6. The tubing set of claim 5, wherein the inner diameter of the second section of the fluid passage is the same as an inner diameter of the tubing.

7. The tubing set of claim 1, wherein the fluid portion and the tine portion are interconnected by a web member.

8. The tubing set of claim 1, wherein the connector fitting comprises a luer fitting.

9. The tubing set of claim 1, wherein the tine passage is tapered from a tine entrance end to a tine exit end.

10. The tubing set of claim 1, wherein the nose piece is formed of a flexible plastic material.

11. An electrosurgical instrument comprising:
    an electrosurgical forceps having at least one tine comprising an electrode connectable to an electrical generator;
    a tubing set connectable to the tine of the forceps, the tubing set comprising:
        a length of tubing extending between a distal end and a proximal end, the tubing formed of a flexible plastic material, a connector fitting on the proximal end configured to connect to a fluid source; and
        a unitary nose piece comprising:
            a fluid portion and a tine portion,
            the tine portion having an elongated tubular tine passage extending therethrough and through which a distal end of the tine of the electrosurgical instrument is slidably insertable,
            the fluid portion having an elongated tubular fluid passage extending therethrough,
            at least a first section of the fluid passage in overlaying alignment with at least a portion of the tine passage, and
            a second section of the fluid passage angled downwardly to direct fluid flowing through the fluid passage toward the tip of the tine when the tine is inserted through the tine passage; and
    the distal end of the tubing inserted into the first section of the fluid passage.

12. The electrosurgical instrument of claim 11, further comprising a further mechanism to hold a portion of the length of the tubing to most of the length of the tine spaced proximally from the nose piece.

13. The electrosurgical instrument of claim 12, wherein the mechanism comprises one or more O-rings circumferentially surrounding the tubing and the tine.

14. The electrosurgical instrument of claim 13, wherein the one or more O-rings are adjustable along the length of the tine.

15. The electrosurgical instrument of claim 11, wherein the fluid portion of the nose piece further comprises a second section of the fluid passage having a smaller inner diameter than the first section of the fluid passage.

16. The electrosurgical instrument of claim 15, wherein the inner diameter of the second section of the fluid passage is the same as an inner diameter of the tubing.

17. The electrosurgical instrument of claim 11, wherein the fluid portion and the tine portion are interconnected by a web member.

18. The electrosurgical instrument of claim 11, wherein the connector fitting comprises a luer fitting.

19. The electrosurgical instrument of claim 11, wherein the connector fitting connects to a source of fluid.

20. The electrosurgical instrument of claim 19, wherein the source of fluid comprises a saline solution.

21. The electrosurgical instrument of claim 11, wherein the tine passage is tapered from a tine entrance end to a tine exit end.

22. The electrosurgical instrument of claim 11, wherein the nose piece is formed of a flexible plastic material.

23. The electrosurgical instrument of claim 11, wherein the tine of the forceps is tapered.

* * * * *

UNITED STATES PATENT AND TRADEMARK OFFICE
CERTIFICATE OF CORRECTION

PATENT NO.       : 7,621,911 B2                              Page 1 of 1
APPLICATION NO.  : 11/412553
DATED            : November 24, 2009
INVENTOR(S)      : John P. Ariola, Jr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 713 days.

Signed and Sealed this

Twenty-sixth Day of October, 2010

David J. Kappos
*Director of the United States Patent and Trademark Office*